(12) United States Patent
Odland

(10) Patent No.: US 6,942,633 B2
(45) Date of Patent: Sep. 13, 2005

(54) SYSTEM FOR TREATING TISSUE SWELLING

(75) Inventor: Rick Mathew Odland, Roseville, MN (US)

(73) Assignee: Twin Star Medical, Inc., Minneapolis, MN (US)

( * ) Notice: Subject to any disclaimer, the term of this patent is extended or adjusted under 35 U.S.C. 154(b) by 300 days.

(21) Appl. No.: 10/104,113

(22) Filed: Mar. 22, 2002

(65) Prior Publication Data

US 2003/0181824 A1 Sep. 25, 2003

(51) Int. Cl.$^7$ .............................................. A61M 37/00
(52) U.S. Cl. ..................... 604/5.01; 604/6.09; 604/6.16
(58) Field of Search ...................... 604/4.01, 5.01–5.04, 604/6.01, 6.09, 6.11, 6.16, 30, 23–24, 500–8, 65; 210/645, 739, 650–52, 762, 790, 85, 90, 195.1–195.2; 128/898–99; 435/1.1–1.2; 73/863

(56) References Cited

U.S. PATENT DOCUMENTS

| | | | |
|---|---|---|---|
| 3,619,423 A | * 11/1971 | Galletti et al. ............... 210/632 |
| 4,235,231 A | 11/1980 | Schindler et al. ........... 128/214 |
| 4,274,417 A | 6/1981 | Delpy ......................... 128/632 |
| 4,340,615 A | 7/1982 | Goodwin et al. .............. 427/2 |
| 4,647,378 A | 3/1987 | Minami ....................... 210/646 |
| 4,726,381 A | 2/1988 | Jones .......................... 128/632 |
| 5,336,164 A | 8/1994 | Snider et al. .................. 604/4 |
| 5,441,481 A | 8/1995 | Mishra et al. ................ 604/29 |
| 5,484,399 A | 1/1996 | DiResta et al. ............... 604/21 |
| 5,501,663 A | 3/1996 | Hattler et al. ................ 604/26 |
| 5,730,712 A | 3/1998 | Falkvall et al. ................ 604/5 |
| 5,865,789 A | 2/1999 | Hattler ........................ 604/26 |
| 6,030,358 A | * 2/2000 | Odland ........................ 604/27 |
| 6,287,608 B1 | 9/2001 | Levin et al. ................. 424/718 |
| 6,537,241 B1 | * 3/2003 | Odland .......................... 604/9 |
| 2003/0187367 A1 | * 10/2003 | Odland ....................... 600/573 |

FOREIGN PATENT DOCUMENTS

WO   PCT/US98/16416   2/1999

OTHER PUBLICATIONS

University of Wisconsin press release dated Dec. 12, 2001, Novel Device Takes Over Where Medicinal Leeches Leave Off (http://www.sciencedaily.com/releases/2001/12/011213084919.htm).

* cited by examiner

*Primary Examiner*—Patricia Bianco
(74) *Attorney, Agent, or Firm*—Fredrikson & Byron, P.A.

(57) ABSTRACT

A system and method for performing site specific therapy to alleviate tissue swelling, involving the placement and use of recovery catheters having semipermeable membranes adapted to recover bulk fluid or fluid components from a tissue site. Fluid recovery can be accomplished by the delivery of a hydratable medium to the membranes, under conditions suitable to permit fluid or components to pass through the membranes in order to hydrate the medium, which is then removed from the tissue site. The method and system can also include the use of components for monitoring the progress of the system, and components for introducing a recovery catheter to a tissue site.

28 Claims, 9 Drawing Sheets

SYSTEM FOR TREATING TISSUE SWELLING

FIELD OF THE INVENTION

The present invention relates to methods and apparatuses for use in treating tissue swelling, including cerebral edema and compartment syndrome. In another aspect, the invention relates to diagnostic and therapeutic methods and apparatuses that include the placement of semipermeable catheters and membranes within the body. In yet another aspect, the invention relates to diagnostic and therapeutic methods and apparatuses adapted to monitor various physiologic parameters in the course of tissue swelling, as well as methods and apparatuses adapted to deliver media, including gases and liquids, to catheters positioned within a tissue. In a final aspect, the invention relates to systems, and components thereof, for recovering fluids from sites of tissue swelling.

BACKGROUND OF THE INVENTION

A number of clinical conditions involve (e.g., are caused by and/or themselves cause) impaired circulation, and particularly circulation within interstitial spaces and within discrete, localized tissues. Among the more vexing examples of such circulatory afflictions are those that involve localized tissue swelling, including compartment syndrome and edema (and in particular, cerebral edema).

Acute compartment syndrome generally involves impaired circulation within an enclosed fascial space (e.g., the anterior compartment of the lower leg), leading to increased tissue pressure and necrosis of muscle and nerves. The soft tissue of the lower leg is contained within four compartments, each bounded by heavy fascia—the anterior, lateral, superficial posterior, and deep posterior compartments. Once diagnosed, the injury requires immediate decompression through surgical release of the skin and fascia covering the area. Other proposed treatment strategies include the use of a sympathetic blockade, hyperbaric oxygen therapy, and treatment with mannitol and/or alloperinol.

Cerebral edema (also known as brain swelling), includes vasogenic cerebral edema (the most common form of edema) which manifests itself in the form of increased permeability of small vessels (breakdown of blood-brain barrier) and the escape of proteins and fluids into extracellular space, especially of white matter. Cerebral edema can be caused by ischemia, loss of oxygen, or focal disruption or loss of blood supply such as stroke. The diagnosis of cerebral edema is based on changes in mental status, imaging, and measurement of intracranial pressure. There remain few conventional treatment options, and they tend to be of limited efficacy.

Monitoring of intracranial pressure (ICP) is considered appropriate for all patients with severe traumatic brain injury (TBI). While the placement of an ICP monitor is invasive, the benefits of ICP monitoring are felt to offset this factor, carry a relatively small risk of complications (e.g., infection, hemorrhage, malfunction, obstruction or malposition), and rarely result in increased patient morbidity. Percutaneous devices (e.g., ventriculostomy catheters) for use in monitoring ICP are commercially available in a variety of styles and from a number of sources. Such devices are commonly placed within the cerebral ventricles, where they enable accurate and reliable monitoring of ventricular pressure and can be used for the therapeutic convective drainage of cerebrospinal fluid ("CSF").

CSF drainage has been described as a potentially effective method of lowering ICP, particularly when ventricular size has not been compromised. CSF drainage typically requires penetration of the brain parenchyma with a ventricular catheter. A variety of ventricular catheters are available for such purposes, e.g., the "MoniTorr" product available from Integra Lifesciences, Inc. As fluid is removed, however, brain swelling often progresses to the point where the ventricular system is compressed and the ability to drain CSF can be compromised. This may be exacerbated by overdrainage, leading to the ventricular walls or the choroid plexus actually collapsing in a manner that occludes the orifices of the catheter. The therapeutic efficacy of convective CSF drainage by conventional ventriculostomy catheters, therefore, has been limited to date.

On a separate subject, gases have long been used for various medical procedures. For instance, oxygen is generally used to enriched the atmosphere for patient therapy and procedures, though oxygen is considered a drug and is dispensed by prescription. High-pressure oxygen is used for hyperbaric treatment, while in other situations, medical air is inhaled by patients, often through secondary pneumatic equipment. Nitrous oxide provides the first and second stages of anesthesia, while nitrogen itself powers pneumatic surgical tools. Carbon dioxide gas is becoming more common in piped systems as it gains more use in advanced respiratory treatment and operating room procedures. Also helium, and mixtures of helium with oxygen, have been described for the treatment of patients having certain respiratory conditions.

An assortment of references also describe either the delivery or recovery of media, such as gases or hyperosmolar liquids, for various purposes and into various locations within the body. Such references include, for instance, situations in which oxygen is delivered to the body by means of catheters positioned within the blood, as well as those in which gases are themselves measured within bodily fluids. See, e.g., U.S. Pat. No. 4,274,417 (Instruments for use in the measurement of gases in body fluids); U.S. Pat. No. 4,726,381 (Dialysis system and method); U.S. Pat. No. 4,340,615 (Apparatus for analysis of absorbed gases); U.S. Pat. No. 5,865,789 (Percutaneous oxygenator for inducing a retrograde perfusion of oxygenated blood); U.S. Pat. No. 5,336,164 (Intravascular membrane lung apparatus); and U.S. Pat. No. 5,501,663 (Inflatable percutaneous oxygenator with transverse hollow fibers).

See also Levin, et al. U.S. Pat. No. 6,287,608, which describes a method and apparatus for the treatment of congestive heart failure by improving perfusion of the kidney by infusion of a vasodilator.

On yet another subject, medical-surgical vacuum and drainage systems exist in the art as well. For instance, the American Society for Testing and Materials provides standard specifications (F960-86(2000)) for medical and surgical suction and drainage systems that include applications such as oral, nasal and tracheal suction, gastrointestinal drainage, pleural space and mediastinal drainage, and closed wound drainage. Other examples, though not included within this specification, can include drainage by the use of catheters and similar instruments inserted into tissue sites, syringes, breast pumps, dentistry suction, and waste gas scavenging. See, for instance, the Mini VAC (Vacuum Assisted Closure) device, available from KCI (San Antonio, Tex.). The VAC device provides negative pressure therapy for the treatment of chronic and acute wound, and allows for the measurement and monitoring of therapy at the wound site through micro-processor control and multi-lumen tubing. In use, the negative pressure is applied to a special dressing positioned in a wound cavity or over a flap or graft.

The pressure distributing wound dressing, in turn, is said to help remove fluids from the wound.

In a more recent approach, a "mechanical leech" has been developed, with the intent of attaching to a wound site in order to remove blood and promote wound heeling. See, for instance, the University of Wisconsin press release dated Dec. 12, 2001, "Novel Device Takes Over Where Medicinal Leeches Leave Off".

See also U.S. Pat. No. 5,484,399, which describes a method and apparatus for reducing interstitial fluid pressure in tissues, particularly in tumors, by applying suction to the interior of the tissue. The method comprises inserting into the tissue one or more needle-like, elongated tubes, each having at least one hole at or near the end that is inserted into the tissue and each having means to apply suction to the protruding end. Components may be provided to measure the pressure within the tissue and to use this measurement to control the suction applied to the tissue through the tubes.

A variety of references describe the placement and use of semipermeable membranes within the body. See, for instance, Mishra (U.S. Pat. No. 5,441,481) which describes a microdialysis probe arranged to have a primary (e.g., electrical) probe secured to it to enable both the microdialysis and primary probe to be extended as a unit for selective sampling and/or administration of compounds to the body. The microdialysis probes are quite large, said to be on the order of 3–4 mm in diameter. Although the reference makes passing reference of the possible "therapeutic application" of their probe, e.g., at column 9, lines 6–20, the suggested delivery of a viscous dextran solution would seem to require the application of tremendous pressures. Moreover, the passage of water through the semipermeable membrane is taught as occurring via chemical (osmotic) means, as compared to water passage brought about by mechanical means, as the result of hydrostatic forces.

Applicant has also previously described methods and related systems for use in site specific therapy of a tissue site. See issued U.S. Pat. No. 6,030,358 and published PCT application No. PCT/US98/16416, the disclosures of which are incorporated herein by reference. In one embodiment, the PCT application provides a system that comprises one or more catheters adapted to be positioned within the tissue site and a delivery/recovery mechanism for employing the catheter(s) to control the movement of bulk fluids and/or active fluid components within or between tissue portions or adjacent tissues in a manner that achieves a therapeutic effect. The catheter(s), in turn, can comprise one or more semipermeable microcatheters, adapted to effect the movement of fluid or fluid components within the tissue site by microdialysis within the tissue site. In its various embodiments, the system previously described by Applicant can be used for the treatment of a variety of disorders, including cerebral edema and compartment syndrome.

In yet another embodiment, Applicant's PCT application describes an apparatus for performing site specific therapy in the event of cerebral edema, the apparatus comprising one or more catheters, each comprising one or more semipermeable membranes, adapted to be positioned in the parenchymal portion of the brain, and adapted to be flowably connected to a source of negative pressure sufficient to remove fluid from the brain in order to alleviate intracranial pressure.

While the embodiments of Applicant's US patent and PCT application remain viable, and valuable, options for various applications, it has become clear that continued efforts, and alternative approaches, are in order with respect to the treatment of tissue swelling, and particularly cerebral edema, as well as compartment syndrome.

SUMMARY OF THE INVENTION

Figure 1:
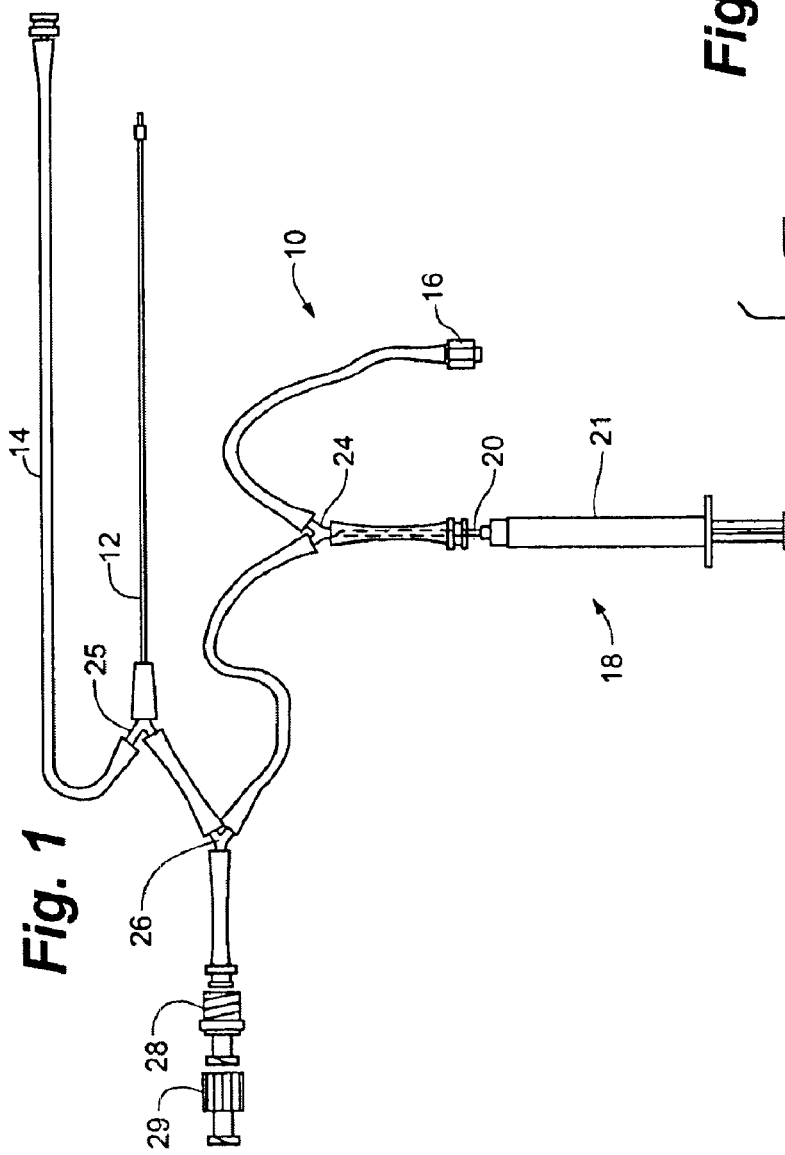
FIG. 1 shows components of a system of the current invention, including a pressure monitor associated with a semipermeable membrane catheter, for use in treating compartment syndrome.

A system of the present invention provides an integrated combination of features and functions for use in the therapy of tissue swelling, including edema and compartment syndrome. A preferred system comprises one or more recovery catheters comprising semipermeable membranes, in combination with recovery components for recovering bulk fluid or fluid components through the semipermeable membranes, and a hydratable medium, preferably in the form of a hydratable gas, adapted to be delivered to a lumen provided by the membranes under conditions suitable to remove water from the environment surrounding the membranes. The membranes can be positioned in any suitable position with respect to a tissue exhibiting swelling, including directly within the tissue itself, within a remote tissue (e.g., circulating blood) having an indirect physiologic effect on the tissue exhibiting swelling, or externally to the body itself, as in the form of a remote unit functionally connected to the body, as by a fluid (e.g., hemofiltration) flow circuit, and in turn to the swollen tissue site. Optionally, the system also includes one or more introducing components, as described further herein.

In a particularly preferred embodiment, where the catheters are positioned directly or indirectly within a tissue site exhibiting swelling the system comprises:

a) one or more recovery catheters comprising semipermeable membranes, each of such semipermeable membranes being preferably in the form of a hollow fiber, b) recovery components for recovering bulk fluid or fluid components (e.g., water) through the semipermeable membranes and from the tissue site, in order to achieve a therapeutic result, preferably in the form of a reduction in swelling, and either c) a hydratable medium, e.g., filtered or dehydrated gas, adapted to be delivered to the tissue site and within the semipermeable membrane(s) under conditions suitable to remove water from the tissue site in the form of hydrated medium, or d) one or more components of a monitoring system associated in an integral fashion with the recovery catheter(s).

In a particularly preferred embodiment, the system provides one or more introducing components adapted to position the recovery catheter(s) within a tissue site, and preferably directly within a site exhibiting swelling. In a further preferred embodiment, the system includes the hydratable medium of feature (c) above, and even more preferably it includes both features (c) and (d) in combination.

DETAILED DESCRIPTION

The present invention further provides a method of preparing such a system by the fabrication and/or combination and functional assembly of its various components, and a method of using such a system to achieve a therapeutic result, as well as various components and subcombinations thereof, several of which are considered to be novel in their own right. The system and method can be used to directly or indirectly treat a tissue site exhibiting swelling.

When used to directly treat a site of swelling, for instance, the semipermeable membrane(s) will typically be positioned within a region that itself exhibits swelling. When used to indirectly treat a site of tissue swelling, the semipermeable membrane(s) can instead (or in addition) be positioned and used in a site remote from (including externally to), but physiologically associated with, the swollen tissue. For instance, the system can be used to dehydrate tissue fluids, such as blood (e.g., intravascularly) or CSF (e.g., intraventricularly), that are physiologically associated with swollen tissue, leading to dehydration of those tissues as well, and ultimately, to a reduction in swelling. The system can be used for the removal of excess fluid in a variety of situations, including pulmonary edema, congestive heart failure, acute renal failure, ischemic heart disease, as well as in cerebral edema and compartment syndrome.

A recovery catheter of this invention comprises at least one, and preferably a plurality, of semipermeable membranes. As used herein, the term "semipermeable membrane" will generally refer to a membrane forming some or all of the wall of a microcatheter (e.g., "hollow fiber"), preferably with a substantially open lumen having at least one open end accessible to liquid or fluid flow within the lumen The membrane portion itself is adapted to permit the passage of bulk tissue fluid or fluid components (e.g., water), while substantially precluding the passage of cells or non-fluid tissue. Such passage can be accomplished using any suitable means, e.g., through pores provided by the membrane itself, as well as by the preparation of membranes having suitable chemico-physical properties (e.g., hydrophilicity or hydrophobicity) to effectively control passage of fluid and its components in a predictable and desired fashion.

The introducing components, in turn, can include any introducing component, or set of components, that is suitable and adapted to position the recovery catheter(s) within a tissue site, and preferably within a site that itself exhibits swelling. Such components can be provided, for instance, in the form of a totally or partially circumferential covering (e.g., stationary or removable delivery sheath), and/or by the inclusion of one or more components (e.g., stylets) positioned internally, adjacent to, and/or along the length of the semipermeable membrane(s) and designed to impart sufficient properties (e.g., stiffness, lubricity) to the overall catheter assembly or portions thereof.

Finally, a system of the current invention includes recovery components for moving and/or recovering bulk fluid or fluid components (e.g., water) through the semipermeable membranes and/or from the tissue site, in order to achieve a therapeutic result at a site of tissue swelling. The movement of fluid or fluid components can be considered to occur in up to at least three modes, including 1) the movement of interstitial fluid within the tissue itself (e.g., by convective flow of interstitial fluid toward a semipermeable membrane positioned therein), 2) the movement of fluid from the tissue and through a semipermeable membrane(s) positioned therein, e.g., by diffusion or convection through the membrane wall and into its lumen), and 3) the movement of fluid from or within the semipermeable catheter(s) (e.g., to a remote site, typically outside the body).

A recovery component of this invention can be provided in any suitable form or combination of forms, including by the use of hydrostatic pressure, diffusion, and combinations thereof, and can be designed to affect any or all of these modes of fluid transport. Hydrostatic pressure, for instance, can be provided as either negative hydrostatic pressure (vacuum or suction) and/or in the form of positive hydrostatic pressure. Diffusion, in turn, can be accomplished using the physical-chemical forces that result from the proximity of two different media, or forces that occur within a suitable membrane positioned at a liquid/gas interface. Such forces result, for instance, in the diffusion of water through the membrane and into the gas, on the basis of either vapor pressure of the liquid itself and/or of liquid components, e.g., volatile compounds such as ketones, as in diabetic coma, or ammonia (including in its various forms, including ammonium hydroxide), as in the course of liver failure.

The system further includes components for providing a hydratable medium or a physiological monitor, or preferably, both. In one preferred embodiment, a system of this invention permits fluid to be effectively withdrawn from the tissue site by the delivery of a medium adapted to be hydrated by, and upon contact with, moisture within the tissue site. In turn, the removal of moisture from the tissue site, upon the removal of hydrated medium, preferably achieves, or contributes to, a therapeutic effect brought about by a reduction in swelling. The word "hydratable", as used in connection with an embodiment of this invention, will refer to a medium capable of being converted from a state of lower moisture content (e.g., lower relative humidity for a gas) to a level of detectably greater moisture content ("hydrated"), by the accumulation of water (e.g., in the form of vapor or liquid) from within the tissue.

The present invention provides a method and system for the delivery of a medium to a tissue site, under conditions suitable to permit the medium to be hydrated by moisture, e.g., within the tissue site, in order to achieve a therapeutic effect upon the withdrawal of hydrated medium from the site. In a particularly preferred embodiment, the medium comprises a gas that can be delivered in a relatively less hydrated (e.g., desiccated or tending toward desiccated) form, and recovered in a more hydrated (e.g. saturated or tending toward saturated) form.

In both such embodiments, the medium is preferably delivered within one or more semipermeable interface materials, preferably in the form of membranes or catheters (e.g., hollow capillary fibers), each having a lumen formed, in whole or in part, by wall portions adapted to permit the accumulation of moisture (and optionally, small solutes), between the tissue and the lumen, while substantially preventing the unrestricted flow of bulk fluids therebetween. One or more catheters are used to form an insertable catheter assembly that can include associated protective and/or placement catheter portions, and conduits providing lumen for the delivery and/or recovery of hydratable gas, as well as negative pressure.

The system of this invention, and corresponding catheter assemblies, can be designed to permit the hydration of the medium to occur either as the dehydrated medium is traveling toward and/or away from the distal catheter tip, and to a distal air plenum. In each case, typically a single impermeable lumen will serve to transfer the gas in the opposite direction, e.g., to return hydrated gas from the plenum or deliver dehydrated gas to the plenum, respectively.

The catheter(s) can be provided in any suitable form and configuration, e.g., as one or more closed and/or open ended individual fibers, as a plurality of closed and/or open ended parallel fibers, and/or as circuitous loops of fibers. In such configurations, the lumen of each catheter will typically include an entry orifice for the delivery of hydratable gas and a recovery orifice for the recovery of hydrated medium from the lumen.

The fibers can be delivered to the tissue site using any suitable introducing components, e.g., they can be positioned within a surrounding placement catheter (e.g., conventional ventricular catheter or customized introducer) that can itself be removed or permitted to remain in place in the course of using the delivery/recovery catheter. Optionally, or in addition, the delivery/recovery catheters can be accompanied by one or more delivery guidewires, stylets, or trocars, and combinations thereof, e.g., adapted to position the semipermeable membrane(s) within the tissue site.

An apparatus and system of this embodiment finds particular use in the treatment of cerebral edema. While not intending to be bound by theory, it appears that an increase in brain tissue water content occurs after brain injury. Osmotic pressure exerted by intracellular osmolarity, estimated to range between 317 and 587 mm Hg in ischemic tissues (Kobari et al., 1985), creates a gradient for the movement of fluid into cells after ischemic injury, leaving large, osmotically active behind in the extracellular spaces (Odland, Sutton, 1999). Such osmotic fluid shifts after ischemic or traumatic injuries may underlie the frequent failure of contemporary therapy to attenuate cerebral edema.

Clearance of edema fluid from tissue to CSF is considered to be a primary mechanism for the resolution of vasogenic brain edema. Hydrostatic pressure gradients are important for fluid movement in the extracellular space, though these hydrostatic pressure gradients become less effective if there is cellular swelling. To date, very few authors have suggested that the manipulation of CSF osmolarity can influence cerebral edema formation after brain injury. See, e.g., Onal et al. 1997, in which the administration of a bolus infusion of albumin into the cerebral ventricles resulted in a significant reduction of tissue water content at 6 hours post injury. Although the effect was transient, and could not be repeated at 24 hours post injury, these results nevertheless support Applicant's suggestion that increasing the osmolarity of CSF after brain injury, by even a small amount, can increase movement of water into the CSF and thus reduce edema.

In one preferred embodiment, therefore, the system of the present invention can be used to counteract the gradient that is thought to result from water movement into tissue, and following injury. Water can be directly and effectively removed from within the cerebral ventricles, and indirectly from the tissue, to decrease tissue edema. With the removal of water from the ventricles, by vaporization into a hydratable gas, fluid can be pulled from the edematous brain tissue. If water vaporization rates do no exceed tissue edema reduction rates, the osmolarity and colloid osmotic pressure of the CSF will remain constant. With such a method, both crystalloid and colloid osmotic pressure can increase, in a manner sufficient to maximize the relative effects of both types of pressure in the reduction of edema.

The system of the present invention also preferably provides a hydratable medium, suitable for use in removing water or volatile compounds (e.g., ketones or ammonia in its various forms) from the lumen of hollow fibers. Any medium that passes through the lumen of the hollow fibers can sweep the vapor clear. The rate of flow of the transport media can affect removal, as can water capacity of the media. Gaseous media have much greater flow rates for similar pressure gradients, and are typically more preferred for many embodiments of the present system.

Several gases can be used to sweep away vapors from within the lumen of hollow fibers of the present invention. The selection of a suitable gas can include consideration of both the effect of the gas on the tissues, and the physical properties of the gas itself. With respect to tissue effect, a suitable gas for use in this invention preferably has no deleterious effect on tissue, under the conditions of use. Rather, the gas is either inert with respect to tissue, or can have a favorable effect, such as the effect of oxygen in improving oxygenation of the tissues. Carbon dioxide is typically less preferred, particularly under conditions where it might increase acidosis, but it may also have some vasodilatory effects that may be beneficial.

A gas suitable for use in the system of this invention preferably also provides an optimal combination of physical properties, including chemical inertness and stability, water content, and the ability to be provided in sterilized form. Air is readily available, and can be dehydrated and filtered for sterility. Nitrogen is inert, commonly available, and as a compressed gas would be of low humidity. Helium is an inert gas with very low density, and thus low resistance to flow. High flow rates can be achieved while maintaining low Reynolds numbers. Those skilled in the art will also appreciate the manner in which temperature will affect the humidity of all gases, and a resistor to drop pressure may also be used.

In addition to water, other volatile compounds may be removed from, or delivered to the tissue, in order to achieve a therapeutic effect using a system of this invention. Examples include removal of ketones in diabetic coma, removal of ammonia in hepatic coma and liver failure, and removal of urea in renal failure. Similarly, mixtures of hydratable gases can be used in order to effectively deliver beneficial agents, such as nitric oxide or oxygen, to the tissue site.

Suitable monitors include, but are not limited to, those adapted to qualitatively and/or quantitatively assess various parameters, preferably in a substantially "real time" fashion during and in the course of using a system of this invention. Such parameters can include physiologic parameters associated with the tissue itself, as well as performance parameters associated with the function of the system or its components. Examples of suitable physiologic parameters include, but are not limited to, tissue pressure (total and partial pressures), blood flow, hydration (water content), temperature, pH, and biochemical parameters (e.g., myoglobin levels).

Such parameters can be determined using any suitable means, for instance, pressure can be determined using conventional fluid column techniques (e.g., diaphragm or manometer), or fiberoptic techniques, while fluid (including blood) flow can be determined using near IR spectroscopy and laser Doppler techniques, and tissue hydration can be determined by a variety of means, including the placement of a suitable probe or electrode to determine electrical impedance.

In a particularly preferred embodiment, the monitoring components are "associated" with the system of this invention, in the sense that one or more portions of the monitoring components are physically and/or functionally integrated with the placement and/or operation of the semipermeable membrane component. As shown in the preferred embodiments of FIGS. 1–4, for instance, the overall catheter assembly is configured to provide a fluid column component for the determination of tissue pressure. Typically, the associated components of such monitoring components will in turn be used with other, conventional, components, such as conduits, connectors and monitors. For example, the Figures depict the manner in which components of a conventional pressure monitoring system (available from Stryker) can be readily adapted for use with a system of this invention.

When used for the treatment of cerebral edema, a system of the present invention can include monitoring components for a variety of parameters. In a preferred embodiment, the parameter is that of intracranial pressure or ICP. In adults, the average ICP ranges from 0–10 mm Hg. 20 mm Hg is considered to be the maximal upper limit of tolerable ICP and pressures exceeding 40 mm Hg are considered extremely elevated. The type of monitor used is dependent on a number of clinical factors, not the least of which is the neurologic disease causing the pressure increase.

Suitable materials for use as semipermeable membranes of the present invention provide an optimal combination of such properties as mass transfer properties, biocompatability, surface-to-volume ratio, processability, hydrophobicity and hydrophilicity, strength, transport rate, and porosity. Examples of suitable hollow fibers are described, for instance, I. Cabasso, "Hollow-Fiber Membranes", pp 598–599 in *Kirk Othmer Concise Encyclopedia of Chemical Technology*. In a preferred embodiment, such membranes are provided in the form of "hollow fibers" or "microcatheters", having walls (or portions thereof) formed of such membrane material. In alternative embodiments, the membranes can be provided in any suitable form or configuration, e.g., in the form of pleated or corrugated membrane sheets, and the like, preferably positioned within and/or by a recovery catheter. In situations where the semipermeable membrane(s) are provided in other than circumferential (e.g., fiber) form, the hydratable medium can be delivered to a major surface of the membrane, opposite the surface in contact with, or accessible by, the tissue fluid itself.

The dimensions of a hollow fiber will depend largely on the intended use of the apparatus. In a number of preferred embodiments, a hollow fiber will be provided in the form of a capillary having an outer diameter of between about 0.1 mm and about 10 mm, preferably between about 0.2 mm and about 3 mm, and more preferably between about 0.3 mm and about 1 mm. Such capillary fibers preferably also provide a substantially open lumen, defined by an inner fiber diameter that is typically on the order of 50% or more, and preferably 70% or more the corresponding outer diameter.

Such membranes preferably also provide permeability cutoffs suitable for use in the intended application. The permeability of hollow fiber membranes for use as microdialysis fibers is generally phrased in terms of kilodaltons (and can range between about 10 kD to about 1000 kd). By comparison, the permeability of fibers used for ultrafiltration is typically considerably greater, and hence phrased in terms of microns, with typical ranges from about 0.1 micron (corresponding roughly to the 1000 kD cutoff at the higher range above) to about 1 micron. Fibers suitable for use in the system of the present invention, therefore, typically provide permeability in the range of from about 1 kD to about 200 microns, preferably from about 10 kD to about 10 microns, and more preferably between about 50 kD and about one micron.

Permeability can be determined using suitable techniques, such as conventional wet sieving techniques. See, for instance, Spectrum Laboratories, Inc. product information which describes the manner in which both the membrane molecular weight cut-off (MWCO) and pore size are related and can be determined.

Hollow fiber performance can be characterized by the molecular weight at which 90% of the solute will be retained (prevented from permeating) by the membrane. This value is called the Molecular Weight Cut-Off (MWCO), which in turn is described as the molecular weight of the largest globular protein that can pass through the pores of the membrane. In general, proteins that weigh more than the MWCO will be retained by the membrane. In addition to the molecular weight, the permeability of a particular solute is dependent on the shape of the molecule, its degree of hydration, and its charge. Each of these may be influenced by the nature of the solvent, its pH, and its ionic strength.

The molecular weight cut-off (MWCCO) is controlled, in turn, by the size of the pores in the membrane. Separation efficiency is influenced by the pore size distribution and the presence of a substantial number of pores much larger than the average will allow leakage of high molecular weight solutes. Thus, a narrow pore size distribution is highly desirable.

The cross-sectional structure of such membranes is either symmetric or asymmetric depending on the type and use. Symmetric membranes, such as dialysis tubing, have pores of the same diameter throughout their thickness while asymmetric membranes, such as unsupported flat sheets, have smaller pores that control the MWCO in a very thin layer or skin at one surface and larger pores in the remainder. The pore size distribution is equally important in the two types.

Sample flow perpendicular to the membranes, renders the membrane susceptible to blockage. The phenomenon can be reduced by sample mixing during filtration. Mixing can be achieved by either stirring or by passing the sample parallel to the membrane.

Semipermeable hollow fibers suitable for use in the system of the present invention can be prepared using conventional methods, and are available commercially. Hollow fibers are typically provided in the form of minute tubules, the entire walls of which are constructed of a semipermeable material. The material, in turn, will typically determine what can or cannot pass through the wall of the tubules. The selection of hollow fiber material is based primarily on the size of molecules to be removed or retained, as well as other physical properties.

By comparison, reverse osmosis (RO) membranes have even smaller pores than either microdialyis or ultrafiltration.

RO membranes are used for removing salt from water, and purifying water. The pores are small enough that only water can pass through (a hydrated water molecule being approximately 0.04 microns diameter). With the small pore size, water flux through the membrane is also limited. For purposes of the present invention, RO membranes are generally less preferred, however, if only in view of their limited availability.

Yet other membranes suitable for use in the present invention have no pores. Water vapor and other gases will pass through very thin silicone or other material. Water goes into vapor phase and diffuses through the membrane. The key to removal of water with this method is to sweep the water vapor from the lumen of the semipermeable membrane by high velocity airflow. Yet other membranes used for water vapor removal do have pores, but the pores do not allow liquid water to pass. Pores in hydrophobic materials do not wet, for instance, but instead allow vaporization at the liquid water-vapor interface within the pores.

Such hydrophobic materials can be provided, for instance, in the form of microporous hydrophobic membranes (MHMs), of the type described in Goldberg et al., "Design Solutions Using Microporous Hydrophobic Membranes", Medical Devices and Biomaterials Magazine 1997 (http://devicelink.com/mpb/archive/97/03/002.html). Numerous polymers can be employed to form MHMs. Today, the predominant polymers used are PTFE (polytetrafluoroethylene), polypropylene, PVDF (polyvinylidene difluoride), and acrylic copolymers. All of these polymers can be treated in order to obtain specific surface characteristics that can be both hydrophobic and oleophobic (repelling liquids with low surface tensions).

The Goldberg et al. article describes the manner in which MHMs block liquids, while allowing air or gases to flow through the membrane. The low surface tensions of MHMs cause them to repel fluids from the surface, leaving the pores of the membrane filled with air. The porosity of the membrane allows air to flow freely through the material. Because of their diverse surface tensions and microstructures, membranes made from various polymers have significantly different properties, including chemical inertness, water-entry pressures, airflows, and surface release characteristics. The hydrophobic nature of an MHM prevents fluid from passing while allowing air to flow freely across the membrane, facilitating accurate pressure measurements.

Those skilled in the appropriate art will understand the manner in which the choice of a particular MHM will depend on a number of design considerations, and will include such considerations as fluid containment, fluid surface tension and fluid pressure. Other considerations, of particular relevance to the present invention, will include airflow rates, surface area, temperature, sterilization method (e.g., MHMs can be sterilized by autoclaving, ethylene oxide, or gamma irradiation), life expectancy, biocompatibility and chemical compatability, as well as membrane quality and consistency.

There are many parameters used to characterize the functional attributes of specific MHMs. Listed below are some of the key terms and their definitions:

Water-Entry Pressure (WEP). Also known as water breakthrough, WEP is the pressure required to force water through a hydrophobic structure. This property is typically expressed in pounds or bars per square inch.

Gurley Value. This variable provides a reliable measure of the airflow through an MHM. Usually expressed in seconds, the Gurley value will describe the length of time a specific volume of air under a specific pressure takes to pass through a specific area of an MHM.

Bubble Point. Used to characterize the MHM's reference pore size, the bubble point is the lowest pressure that is required to displace a low-surface-tension fluid from the pore structure of an MHM, and is typically expressed in pounds or bars per square inch.

MHMs can be sealed to plastic devices using several different methods. Depending on the device material and the polymer makeup of the MHM, alternatives can include ultrasonic welding, radio-frequency (RF) sealing, heat sealing, insert molding, or adhesive bonding.

Those skilled in the art, given the present description, will appreciate the manner in which water vaporization can depend on several factors, including airflow velocity and temperature dependence. Water vapor pressure is directly dependant upon temperature. Water vapor pressure at room temperature is 17 mmHg, while at body temperature it is 47 mmHg. The selection of hollow fiber material can depend upon the molecular species to be removed and/or to be retained. Typically selection is made of a suitable pore size corresponding to the size of the molecules, and particularly biomolecules, keeping in mind the manner in which molecular charge, shape, and other factors can play a role as well, under the particular conditions of use. Generally, water, salts, and/or proteins are targets for removal using a system of this invention, while cells and tissue segments are retained.

In a preferred embodiment, the system of the present invention accomplishes the removal of water, by tissue ultrafiltration, as a therapeutic treatment. Removal of only water can be accomplished by use of RO membranes or water vaporization. Water, salts, and some proteins can be removed by membranes having permeability in the range of conventional microdialysis fibers. All molecules, including large proteins can pass through fibers having the characteristics of conventional ultrafiltration probes.

The removal of only water will increase the osmolarity of the fluid left behind, while the removal of water and salts will increase the colloid osmotic pressure of fluid left behind. Tissue osmolarity will be maintained by the water that is transmitted through the corresponding tissue. Increasing the osmolarity of extracellular fluid, or preventing a decrease in osmolarity, will have the effect of improving convection and diffusion in a tissue. These effects will improve edema removal, and can also be used to advantage for drug delivery. Suitable drugs for delivery in this manner include, for instance, neuroprotectant agents, antimicrobial agents (e.g., antibacterials and antivirals), vasodilators (e.g., nitric oxide), anticoagulants, genetic vectors, and anti-inflammatory agents (e.g., steroids for the treatment of compartment syndrome).

Hollow fibers suitable for use in the present invention provide an optimal combination of other properties as well, such as inner diameter, outer diameter, wall thickness, tensile strength, compressive strength, and transmembrane conductance. Collectively these properties are suitable to provide the fiber with the ability to withstand positive or negative pressure. Transmembrane conductance is a measure of the ability to transmit water and other substances. High transmembrane conductance is seen in large pore fibers.

These fibers can be used singly or can be grouped into bundles, e.g. containing anywhere from a plurality to several hundred or even several thousand such fibers. In most cases, a hollow fiber will be used as a cylindrical membrane in a manner that permits selective exchange of materials across its walls. Optionally, such fibers can be used in varying combinations, such as coaxial fibers having differing permeabilities to oxygen, cells, and fluid or its components. Such combinations can be designed and used to provide a sequential selectivity with respect to fluid flowing sequentially through the fibers or fiber portions.

semimpermeable regions in particular tissues or areas thereof.

Suitable membranes are available commercially, including from Applied Membrane Technologies, as their line of "AMT" type membranes, and from Minntech, Inc. Examples of suitable membranes, including the materials and available pore sizes and dimensions, are provided in TABLE I below.

TABLE I

| Source | Material | Pore Size (expressed in kilodaltons (KD) or microns) | ID (mm) | OD (mm) |
|---|---|---|---|---|
| A/G Technology | Polysulfone | 10 KD | 0.25, 0.5, 1 | 0.5, 1, 1.8 |
| Corp. | Polysulfone | 30 KD | 0.5, 1, 2, 3 | 1, 1.8, 3, 4 |
| Needham, MA | Polysulfone | 50 KD | 0.5, 1 | 1, 1.8 |
| | Polysulfone | 0.1 µm | 0.75, 1, 2 | 1.5, 1.8, 3 |
| | Polysulfone | 0.2 µm | 1 | 1.8 |
| | Polysulfone | 0.45 gm | 1 | 1.8 |
| Akzo Nobel | Cellulose | 10 KD | 0.2 | 0.216 |
| Asahi | Polyacrylonitrile (PAN) | 50 KD | 0.25 | 0.32 |
| Corsep | PAN | 50 KD | 0.2 | 0.31 |
| | Polyethersulfone | 0.1 µm | 0.6 | 1.0 |
| | Polyethersulfone | 0.2 µm | 0.6 | 1.0 |
| | Polyethersulfone | 0.5 µm | 0.6 | 1.0 |
| Minntech | Polyethersulfone | 10 KD | 0.2 | 0.28 |
| (Minneapolis, MN) | Polyethersulfone | 30 KD | 0.28 | 0.36 |
| | | 70 KD | 0.2 | 0.28 |
| | Polyethersulfone | 0.05 µm | 0.28 | 0.36 |
| | Polyethersulfone | 0.2 µm | 0.28 | 0.36 |
| | Polyethersulfone | 0.45 µm | 0.28 | 0.36 |
| Spectrum | Polyethersulfone | 0.2 µm | 0.5, 1.0 | 0.9, 1.4 |
| Laboratories | Cellulose | 0.1 µm | 0.64 | 0.86 |
| (Rancho Dominquez, CA) | Cellulose | 0.2 µm | 0.64, 1 | 0.86, 1.2 |

Semipermeable membranes can be prepared in any suitable manner, e.g., by microperforating an otherwise intact capillary or by spinning hollow fiber membranes from natural or synthetic polymers. Such fibers can be formed having any desired characteristics, e.g., isotropic (dense or porous) and anisotropic (assymetric). Examples of suitable materials for use as microcatheters of this invention include, but are not limited to, microinfusion tubing such as polyethylene tubing available from Clay Adams under the designations PE-10 (0.28 mm/0.61 mm, inner and outer diameters), PE-20 (0.38 mm/1.09 mm), PE-50 (0.58 mm/0.965 mm) and PE-90 (0.86 mm/1.27 mm). Such tubing can be microperforated by any suitable means, such as lasers and the like.

Optionally, and preferably, microcatheters used in this invention can have regions of varying characteristics, including varying porosity, rigidity, and the like, for instance those that vary between sequential and adjacent, or suitably spaced, longitudinal sections, or in or any other suitable pattern. Such variations can be used, for instance, in a size exclusion fashion to improve or provide the ability to retain or permit the passage of solutes of varying sizes in a predetermined manner. Such variations can also be used to provide regions of greater rigidity or varying structure (e.g., fluted), in order facilitate their placement in tissue. Such variations can also include the incorporation of means (e.g., radioopaque materials) to facilitate the visualization of implanted catheters. Such variations can also be used to place regions of semipermeable membranes in desired locations within the tissue, e.g., in order to effect a gradient between two or more regions, or to avoid the placement of One or more introducing components are preferably included in a catheter system of this invention and can be provided in any suitable form, e.g., using suitable introducers (typically in the form of one or more sheaths used to facilitate the placement of a catheter through the skin, typically into a vein or artery), guidewires (e.g., typically coiled wires adapted to fit inside a catheter assembly for the purpose of directing the catheter into or through a tissue site), stylets or trocars (e.g., sharp pointed instrument used with a cannula for piercing a vessel or chamber to facilitate insertion of the cannula), and combinations thereof. In turn, the introducing components, including various components, can provide an assembly that is steerable or nonsteerable, useful with open incision or using minimally invasive means, and/or adapted to be dilated, expanded, or compressed, thermally regulated. Optionally, an introducing component can comprise or be provided in the form of a shaped memory alloy, such as Nitinol (NiTi).

The invention will be further described with reference to the Figures, wherein FIGS. 1–4 show a preferred system of the invention for use in treating compartment syndrome, and FIGS. 5–10 show a preferred system of the invention for use in treating cerebral edema.

FIG. 1 shows a catheter assembly 10 that includes an implantable catheter body 12 providing a conduit leading through Y-adaptor 25 to a pressure line and associated connector 14 for attachment to a pressure monitor (not shown), as well as a conduit and associated connector 16 for attachment to a vacuum source (not shown). Within the vacuum conduit, and attached by Y-connectors 24 and 26, are a filtrate collection assembly 18 and filter/cap assembly 28/29, respectively. The collection assembly can take any suitable form, and is here shown as including a syringe collection chamber 21, above which is positioned the proximal end of the incoming portion of collection tube. Also associated with the vacuum conduit is filter/cap assembly 29. With the cap 29 removed, fluid is vented via Y-connector 26 and collected via drip tube 20 and syringe 21.

Figure 2:
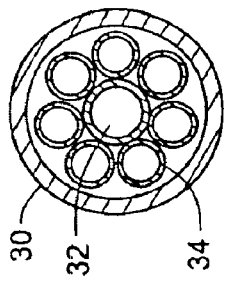
FIG. 2 shows a cross section taken along A—A of the catheter of FIG. 1.

FIG. 2 shows a cross-section taken across A—A of the catheter assembly 12, showing the outer impermeable tube wall 30 of catheter assembly 12, within which are positioned a central fluid filled tube 32 for pressure measurement, and seven circumferentially placed semipermeable membranes 34.

Figure 3:
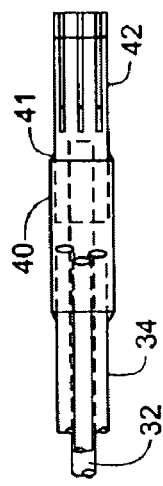
FIG. 3 shows an enlarged detailed view of the distal end of the catheter of FIG. 1.

FIG. 3, in turn, shows an enlarged detailed view of the distal end of catheter assembly 12 as shown in FIG. 1, including the distal portions of semipermeable catheters 34, which are shown terminating within a circumferential collar portion 40 that itself terminates distally in a split end, to prevent constriction by surrounding tissue. In this particular embodiment, the catheters are also closed on their distal ends, within a region of suitable adhesive 44. In the region proximal to collar portion 40, however, the walls of the membranes are accessible for direct contact with surrounding tissue. Also shown is the fluid filled pressure lumen 32, extending distally beyond collar 40 and into the split end 42, in order to provide unimpeded contact with tissue fluid. Adhesive 41 is shown providing a seal between collar 40 and split end 42.

Figure 4:
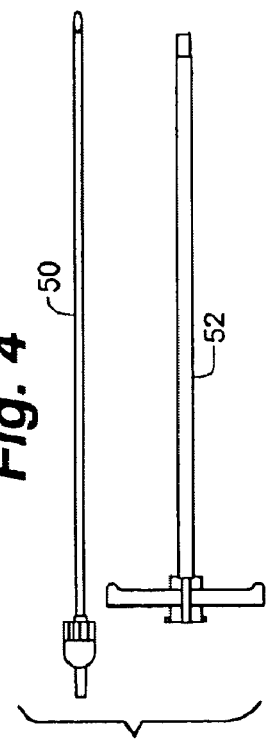
FIG. 4 shows a set of introducer components for use in the system of FIG. 1.

FIG. 4 shows components of introducing components suitable for use with the catheter assembly of FIG. 1, including a trocar needle 50 and split sheath 52. In use, the trocar can be positioned within the sheath, and the combination positioned within the tissue site. Once positioned, the trocar can be removed from the sheath, leaving the sheath in position within the body, whereupon the catheter portion 12 of assembly 10 can be inserted into the sheath. With the catheter positioned, the sheath can be finally removed, leaving the catheter effectively in place within the body. Following use, the catheter assembly can itself be removed from the tissue site, or permitted to remain in place for subsequent use.

In the course of using the system shown in FIGS. 1–4, the vacuum source is operated in order to draw a vacuum through the associated conduit, and ultimately, on the proximal ends of closed membranes 34. In turn, water and permeable solutes are drawn through the membrane walls and into the lumen for removal from the tissue. Simultaneously, the fluid filled, open-ended, central tube can be operated to measure tissue pressure within the split end 42.

Figure 5:
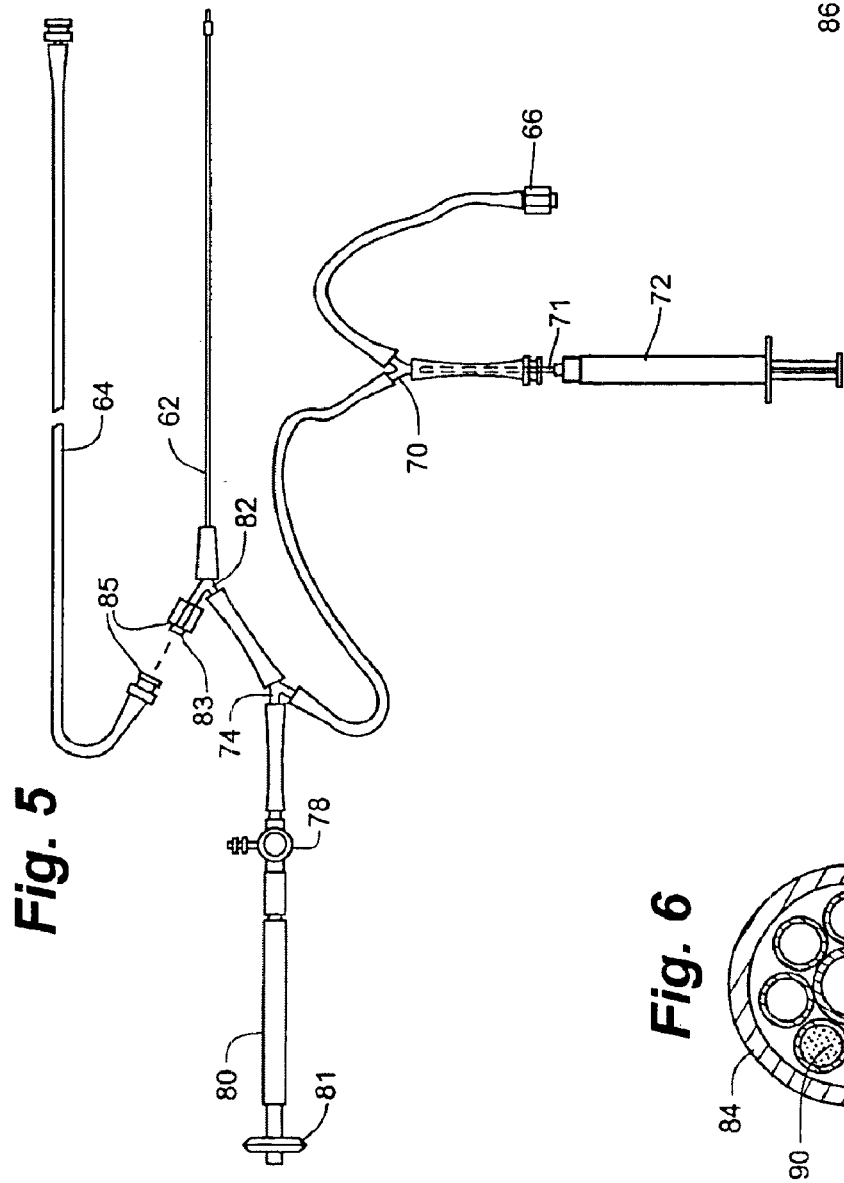
FIG. 5 shows components of an alternative preferred system of the invention adapted to provide a hydratable medium, for use in treating cerebral edema.

Turning briefly to FIGS. 5–10 there is shown a preferred embodiment of a system of the present invention having particular use in the treatment of cerebral edema. FIG. 5 shows a catheter assembly 60 that includes an implantable catheter body 62 that is adapted to be controllably and operably connected (via Y-adaptor 82) with a conduit and associated connector 64 for attachment to a pressure monitor (not shown). The catheter body 62 is also adapted to be controllably and operably connected (via Y-adaptors 82, 74 and 70, sequentially) with a conduit and associated connector 66 for attachment to a vacuum source (not shown). The pressure monitor line provided by conduit 64 further includes a coupling portion 85 near Y-adaptor 82, which is shown in its uncoupled form, to permit the placement of an introducer (e.g., positioning stylet) through the corresponding access aperture 83 and longitudinally down the body of catheter 62.

Attached within the vacuum conduit, via Y-connectors 82 and 74, respectively, are an assembly of components (including stopcock 78, desiccant dryer 80 and an air filter 81) for providing filtered, desiccated air or other suitable gas from a remote source (not shown) to catheter 62. Also attached within the vacuum conduit, via connectors 82, 74 and 70, respectively, are a drip tube 71 and associated syringe collection chamber 72. With stopcock 78 in the open position, air or other suitable gas can be delivered to the catheter distal end positioned within the body.

Figure 7:
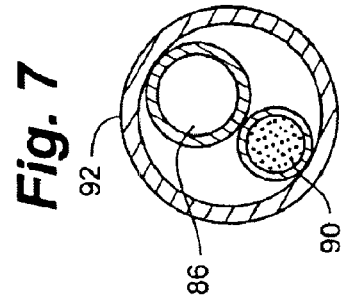
FIG. 7 shows a cross section taken along B—B of the catheter of FIG. 5.
Figure 6:
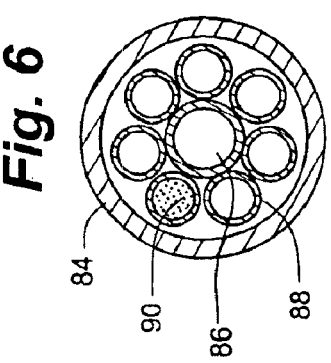
FIG. 6 shows a cross section taken along A—A of the catheter of FIG. 5.

FIG. 6 shows a cross section taken across A—A of catheter assembly 62, including the outer impermeable tube portion 84 enclosing a central inner tube 86, fluid filled for pressure measurement, and six semipermeable membrane catheters 88, as well as an impermeable tube 90 for the supply of desiccated gas. FIG. 7, by contrast, shows a cross section taken across B—B of the catheter assembly of FIG. 5, and shows the outer wall 92 of the Y-connector 82, enclosing the central inner tube 86 adjacent the desiccated gas supply tube 90. The semipermeable membranes, which are located distally from this point, are open-ended on both ends, in order to permit desiccated gas to be delivered via supply tube 90 to their distal ends, and to then traverse the membranes in a proximal direction toward Y-connector 82, becoming hydrated through the walls of the membranes by surrounding tissue.

Figure 8:
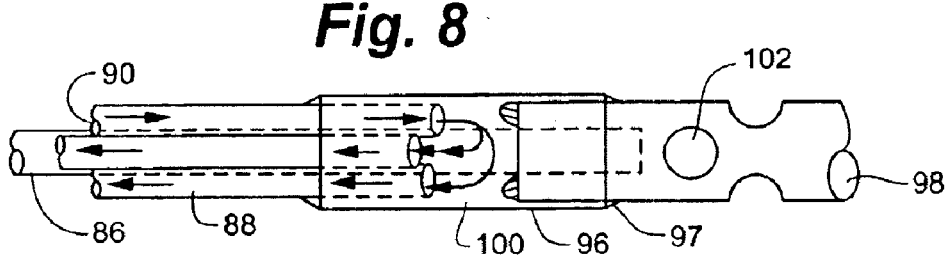
FIG. 8 shows an enlarged detailed view of the distal end of the catheter of FIG. 5.

The operation of the various parts is depicted in FIG. 8, in which the distal end of catheter portion 62 is shown in enlarged detail, as having a collar portion 96 attaching, distally, a soft distal tip 98 (e.g., in an adhered or press fit connection) and attaching proximally the assembled catheters (including membranes 88, air supply tube 90, inner fluid filled lumen 86). The collar provides an open space 100 (plenum) between the distal tip and catheter assembly, for use as an air return chamber. The distal tip is provided with open pores 102 in order to permit free access of surrounding tissue fluids to the catheter tips. The inner fluid filled lumen extends sufficiently into the distal tip to permit pressure determination to be made there.

Figure 9:
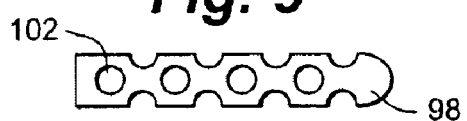
FIG. 9 shows an enlarged detailed view of the soft distal tip of the catheter of FIG. 5.
Figure 10A:
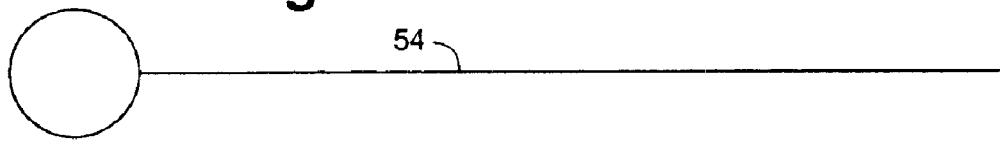
FIG. 10 shows component parts for use in accessing the brain tissue, in order to place the catheter of FIG. 5.
Figure 10B:
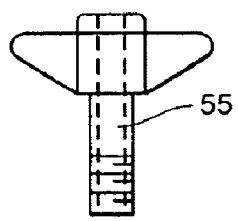
Figure 10C:
Figure 10D:
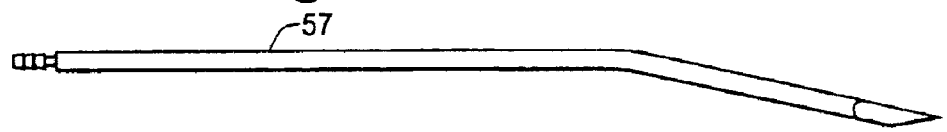

In use, desiccated air (or other suitable gas) is supplied through air supply tube 90 and into the air return chamber, where it circulates in order to enter the open lumen of the semipermeable catheters, and traverse the lumen of those catheters in a proximal direction. With the walls of the membranes in contact with surrounding tissue, the desiccated air can be drawn by the vacuum applied from a proximal direction on the open ended membranes. Simultaneously, the fluid filled inner lumen can be used to determine tissue pressure, by its proximal functional attachment to a suitable pressure measurement device (not shown). As compared to the embodiment of FIGS. 1–4, the membranes of FIGS. 5–10 are open-ended on both ends, to permit the flow of desiccated gas therein. FIG. 9 shows an isolated view of distal tip 98, showing a typical arrangement of access pores 102, while FIG. 10 shows a stylet 104 adapted to be used for assistance in placing the catheter portion 62 of FIG. 5. Optionally, this embodiment can be operated with the stopcock 78 closed to get suction only. As a further optional feature, some (e.g., alternating) fibers can be closed at distal end such that these fibers operate only as suction devices while other fibers have circulating dry air.

FIG. 10 shows an assortment of components adapted for use in preparing the skull and/or positioning a catheter according to FIG. 5. In particular, there is shown a positioning stylet 54 (FIG. 10*a*), self tapping bolt 55 (FIG. 10*b*), burr hole drill 56 (FIG. 10*c*) and tunneling trocar 57 (FIG. 10*d*). In use, the burr hole drill can be used to provide access through the skull and to the parenchymal tissue beneath. The catheter assembly of this invention can be positioned with the stylet and in the desired location directly, by first securing the bolt into the skull, and positioning the catheter assembly therethrough. Optionally, the catheter assembly can be positioned to a site remote from the access hole, by employing the tunneling trocar 10d beneath the skull as sufficient distance under the scalp, then inserting the catheter assembly therein.

Figure 11:
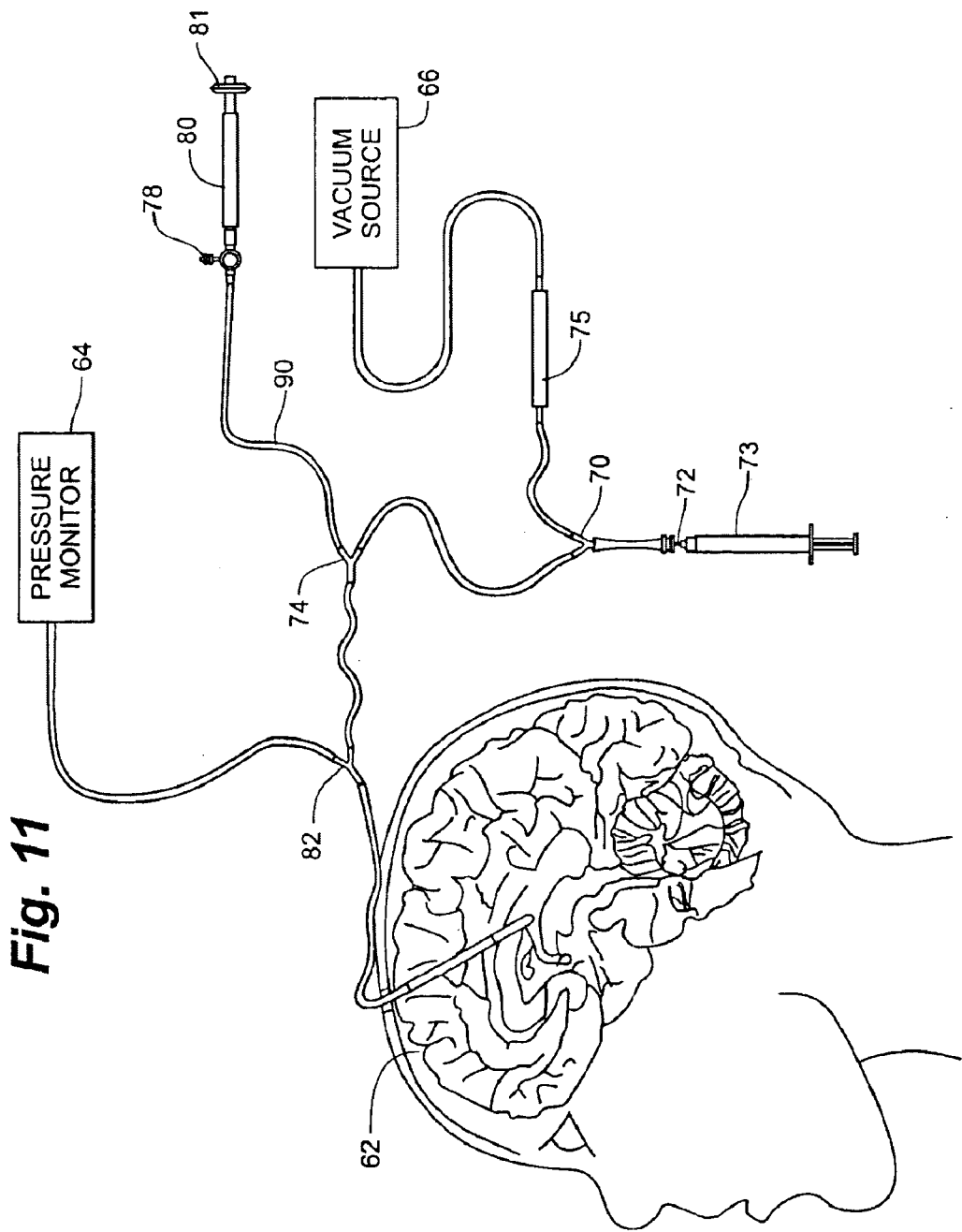
FIG. 11 is a diagram with the catheter shown in position within the brain of a patient.

Finally, FIG. 11 shows a schematic diagram showing the placement and use of a catheter assembly such as that shown in FIG. 5. The catheter is shown positioned within the brain tissue site exhibiting swelling, in a manner that permits the controllable flow of desiccated air from desiccant 80 and through stopcock 78 and into air supply tubes 90 within the catheter body. As the desiccated air travels through air supply tube 90 exiting into the air return chamber at the distal end of the catheter body, where it is drawn into the plurality of open-ended semipermeable membranes. As the desiccated air travels back, proximally, through the membranes, it draws moisture through the exposed portions of those membranes in a manner sufficient to remove water or vapor from the surrounding tissue. Once removed from the body, fluid is drawn toward the collection chamber by vacuum source 66, showing also optional exit desiccant 75, with drip tube 72 providing a suitable trap to permit fluid to be withdrawn from the vacuum line.

As shown in FIGS. 5-11, the preferred system also provides an associated pressure monitor 64 and associated conduits and connectors, which is adapted to be used simultaneously with the delivery and recovery of desiccated gas.

A system such as that shown in FIGS. 1-4 can be used with the following protocol and instructions in order to treat sites at risk for compartment syndrome. Patients considered candidates for prophylactic use of compartment syndrome therapy must meet all of the following criteria:

1. Be at risk for compartment syndrome;
2. Have a single fracture;
3. Have closed or Gustilo grade I open tibial shaft fracture that requires surgical stabilization;
4. Are skeletally mature (generally over age 16);
5. Have no other traumatic injury;
6. Be mentally alert and able to sign patient consent form.

Patients not considered candidates for compartment syndrome therapy include the following:

1. Have fracture currently or previously treated by closed methods (casting, bracing, or splinting);
2. Have grade II or grade III open fractures;
3. Have evidence of CS at the time of admission;
4. Are greater than 80 years of age;
5. Have medical condition(s) which preclude use of indwelling catheters for up to 48 hours;
6. Have co-morbidities that may increase the incidence of compartment syndrome (shock, major abdominal or thoracic trauma, massive soft tissue trauma).

Certain cautions will typically be followed with regard to the use of such a system, including:

1. Care should be taken when inserting the introducer to avoid any nerves or large blood vessels in vicinity of treatment site.
2. Slit tubing tip and hollow fiber bundle are fragile. Care should be taken when inserting catheter into sheath. Damage to the tip may lead to false pressure readings.
3. If the catheter is not located in desired location, remove the catheter and reinsert the introducer to reposition the catheter at new location.
4. To ensure accurate pressure reading, the pressure monitor's transducer diaphragm must be positioned at same height as the tip of the catheter.
5. If any resistance is met when retracting the catheter, inject up to ½ ml of saline and attempt removal again. If resistance is still met, leave the device in place for 30 minutes without vacuum. Attempt removal again, and if resistance is still met, the surrounding skin may need to be released using a #11 scalpel (or equivalent) under local anesthesia.

Figure 12:
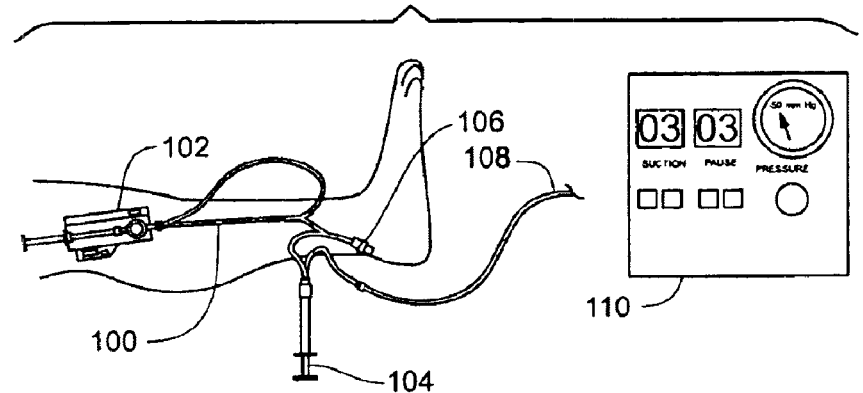
FIGS. 12–21 provide various views and steps arising in the use of a system such as that shown in FIGS. 1–4.
Figure 13:
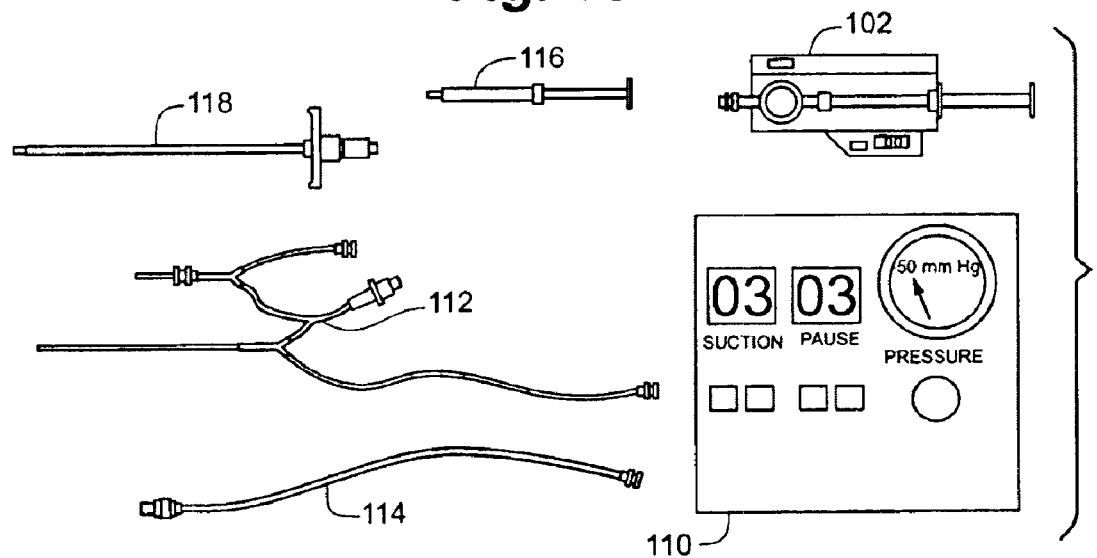

The system is designed to remove interstitial fluid from body muscle compartments while simultaneously monitoring compartment pressure. The goal is to reduce the severity of compartment syndrome by reducing fluid volume while monitoring tissue pressure within the affected muscle compartment. A preferred system and related components is shown in FIGS. 12 and 13, showing the functional arrangement of a CST catheter 100 inserted into a compartment, and including a pressure monitor 102, fluid collection reservoir 104 and vent 106, as well as a line 108 to an intermittent vacuum pump 110. Various components making up a preferred system of this type are shown in FIG. 13 as including the CST catheter set 112 and tubing extension set 114, as well as a 3 cc syringe with cap 116 and introducer 118.

To place the catheter, an introducer, consisting of a Teflon™ sheath over a stainless steel trocar, is initially inserted into the muscle compartment at the site of therapy. After the introducer is positioned, the stainless steel trocar is used as a radio-opaque marker to fluoroscopically verify sheath position. After position is verified, the trocar is removed and the catheter is then inserted through the open sheath lumen. The sheath is then longitudinally split and separated for removal, allowing the catheter to be in intimate contact with the surrounding tissue. The catheter is designed to be in-dwelling for up to 24 hours.

The catheter, in combination with a suitable pressure monitor (e.g., shown here as a Stryker Intra-Compartment Pressure Monitor), can measure the intramuscular pressure during therapy. Optionally, the system can include continuous injection, provided by a syringe pump, in combination with disposable pressure sensors (as currently used for arterial blood pressure measurement) that are adapted to be plugged into standard hospital pressure monitors. To measure this pressure, the catheter's distal tip employs a slit tube to ensure fluid communication with the surrounding tissue. Applicant has discovered the manner in which conventional pressure monitoring systems can be modified so as to permit the infusion of on the order of one to fifty microliters per hour of saline into the fluid column to maintain patency and accuracy.

The catheter has a bundle of seven (7) filtration fibers located near its distal tip. A vacuum pressure of negative 50 mm Hg is applied intermittently to remove interstitial fluid in the vicinity of the catheter. The vacuum pressure "On" and "Off" time is set at (3) three minutes on and (3) three minutes off. After removal, the fluid is collected in a graduated 3 cc syringe with a female luer distal end. Optionally, both the vacuum applied and the timing of vacuum can be adjusted as desired. For instance, such vacuum pressure can be used at between about −1 to about −760 mm Hg, and more preferably between about −50 to about −500 mm Hg. The vacuum pressure can be cycled so as to provide "On" and "Off" cycles at periodic time intervals (e.g., from a few seconds to on the order of 30 minutes "on", followed independently by a few seconds to on the order of 30 minutes off. After removal, the fluid is collected in a graduated 3 cc syringe with a male luer on the distal end.

The system can be provided in the form of one or more individually packaged sterile sets, including an introducer and catheter set, that can be used in combination with one or more other components commercially available in order to provide a compartment syndrome therapy ("CST") system of this invention (e.g., a pressure monitor with associated disposable components, a vacuum pump (e.g., Medela brand), a syringe with cap, and an extension tubing set.

Figure 14:
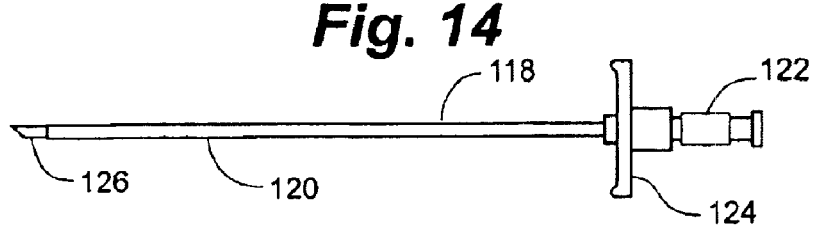

The introducer provides access into the muscle compartment for placement of the CST catheter. As shown, the set consists of a 5 French tear-away sheath placed over a mating stainless steel trocar. After placement and optional x-ray verification, the trocar is removed, the catheter is inserted, and then the sheath's hub and shaft are split longitudinally and removed from the in-dwelling CST catheter. The CST introducer 118 is illustrated in FIG. 14.

The tear-away sheath 120 is composed of a thin-walled plastic tube sized to allow introduction of the 5 French CST catheter. Both the hub 122 and sheath 124 are designed to be longitudinally split for easy removal around the in-dwelling CST catheter. The mating trocar 126 is composed of 304 stainless steel. Its three-(3) facet tip is electro-polished to a sharp point.

The CST catheter set is designed to remove excess interstitial fluid buildup and simultaneously monitor compartment pressure. One or more catheter sets can be used, of the same or different types and in varying positions during the course of treatment. The catheter portion of the set is 5 French in diameter and contains a bundle of seven (7) porous hollow fibers near its distal tip. The fibers remove the surrounding interstitial fluid through both passive drainage and active vacuum. The fluid is collected in a fluid trap located in-line with the vacuum source. The fluid collection port is connected to a 3 cc syringe. A filtered vent is connected to the vacuum line to relieve vacuum when desired.

Figure 15:
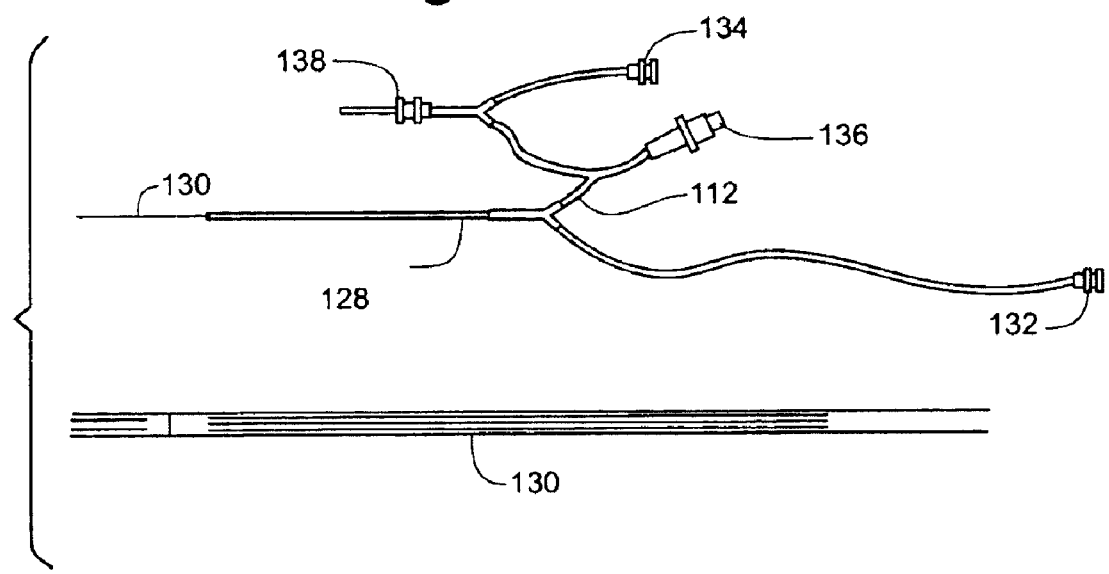

With the vacuum source turned on or off, the catheter supports compartment pressure monitoring by providing a fluid column from the tissue through the slit lumen at the catheter's tip to the external Stryker pressure transducer. FIG. 15 is a drawing of the CST catheter set 112 with its major components identified and a detail drawing of the catheter's tip section.

The catheter body 128 can be composed, for instance, of two coaxial polyimide tubes affixed independently to each of the two Y connector ports, or more preferably, a polyimide outer tube and a stainless steel inner lumen tube to give the catheter more stiffness. The outer tubing is connected to the fibers and is used for fluid drainage. It is fiber reinforced to minimize kinking. The inner tubing is the pressure monitoring lumen. At its distal tip, the inner tubing extends beyond the outer tubing to support the slit tip and ensure fluid communication with the tissue.

Near the distal end of the catheter is a bundle of seven (7) hollow fibers 130. The fibers are porous hollow filters that pass water and interstitial fluid. The active vacuum is applied to the inside lumen of the filters. The fluid is drawn from the surrounding tissue, through the fibers, out the vacuum lumen and into the fluid collection syringe.

The pressure monitoring line 132 is connected to the inner tubing. The female luer at its proximal end is connected to a Stryker Pressure Monitoring device. The line is fluid filled to maintain communication with the Stryker device. The Stryker Intra-Compartmental Pressure Monitor System is indicated for use on compartment syndrome. Stryker Instruments (Kalamazoo, Mich.), Pressure Monitor (part # 295-1), quick pressure monitor set (part # 295-2), normal saline syringe (3 cc NaCl Fill/Syringe, part # 295-5), and quick pressure monitor pack (part # 295-2, including side ported needle, 18 ga.×2.5 inch and diaphragm chamber.)

The vacuum line 134 is connected to the catheter's outer tubing. The female luer at its proximal end is connected to the vacuum pump. A vent 136 with a 0.2-micron filter is attached to the vacuum line. The vent is normally closed and can be opened to relieve vacuum pressure by removing the attached cap. The fluid collection line is connected to the vacuum line. The female luer at its proximal end along with the protruding drip tube 138 are inserted into a 3 cc syringe acting as a sample collection reservoir. Sterile 3 cc syringe with cap (Becton Dickinson, Franklin Lakes, N.J.), part # B-D, 3 ml Luer-Lok™ syringe.

Figure 16:
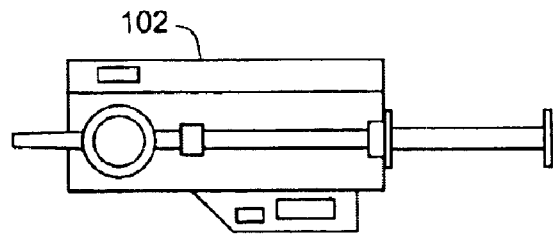

The Stryker Intra-Compartment Pressure Monitor is a hand-held, portable pressure monitor specifically designed to measure intramuscular pressures. A complete description of the device and its associated disposables, the diaphragm chamber and saline filled syringe, are described in its instruction for use provided by Stryker. See the monitor 102 in FIG. 16, in the form of a Stryker Pressure Monitor, Model 295-1 with disposable diaphragm chamber and syringe.

The vacuum pump is used to control the vacuum pressure, the "suction" interval, and the "pause" interval. The pump is connected to the catheter set's vacuum line. A suitable pump is manufactured by Medela, Inc. (McHenry, Ill.) as model 046. The Medela Pump meets Class IIa medical product basic requirements in accordance with Appendix 1 of the Council Directive 93/42/EEC Governing medical products. Pump Setting Ranges

| Vacuum Pressure | 0–55 mm Hg |
| Suction Time | 0–99 minutes in 1 minute steps |
| Pause Time | 0–99 minutes in 1 minute steps |

A standard sterile 3 cc syringe with a female luer fitting is used as the fluid reservoir. It can be easily attached to the catheter set's fluid collection port. A standard sterile extension tubing set is used to connect the vacuum line to the vacuum source, e.g., as available from Medex (Dublin, Ohio), as part # # 536040 (60 in/152 cm Mini Vol. Ext. APV 0.3 ml). Specific length is dependent on the pump location. The tubing set is supplied sterile in a pouch. It comes with one male and one female luer connector with protective caps.

Prepare catheter for placement following standard wound care practice. Connect the syringe to the catheter's fluid collection port. Set the syringe plunger to approximately the 2 cc graduation, and connect the sterile 3 cc syringe to the fluid collection port. Connect the catheter to the transducer, following instructions provided by the manufacturer. Connect the pressure monitoring line to the pressure monitoring device. Prime the pressure monitoring line, leaving the CST catheter's protective cover in place until the catheter is ready for implantation.

Figure 17:
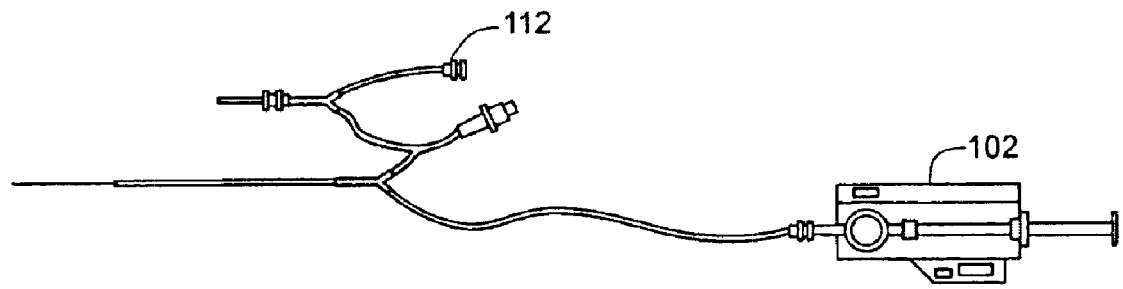

When connected, hold the catheter above the monitor pointing the catheter's distal tip up from horizontal at a 45-degree angle. Slowly flush fluid from the Stryker syringe until a steady stream of fluid is observed flowing from the catheter. FIG. 17 provides a diagram for the connection of the syringe and pressure line priming using the assembly 112 and pressure monitor 102.

Set vacuum pump PRESSURE, SUCTION Interval, and PAUSE Interval (reference vacuum pump instruction for use provided by the manufacturer.)

Figure 18:
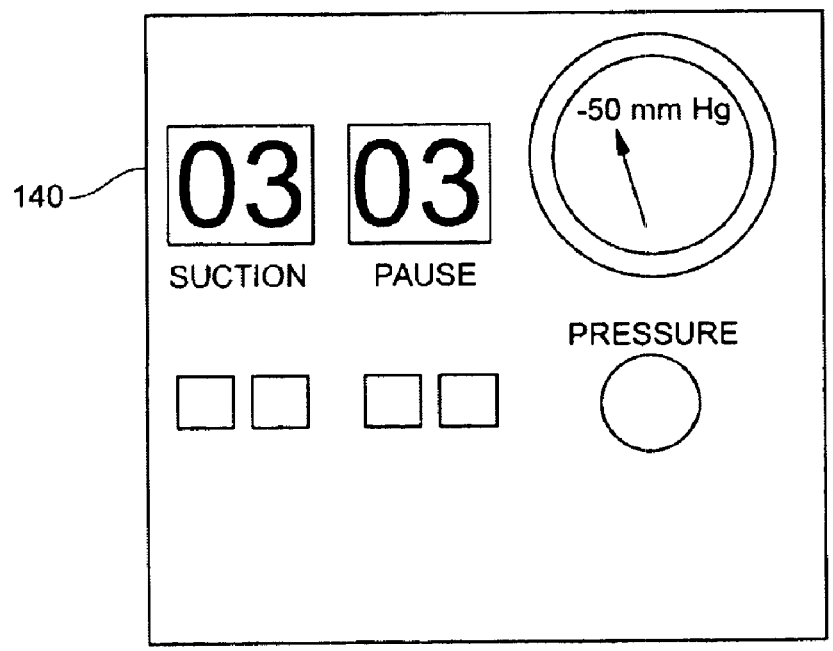

1. Set vacuum pump pressure. Adjust the pump's pressure control knob to −50 mm Hg+/−5 mm Hg.
2. Set SUCTION Interval. Adjust the pump's "Suction Time" to 03 minutes.
3. Set PAUSE Interval. Adjust the pump's "Pause Time" to 03 minutes. (See FIG. 18 for pump settings 140).
4. Monitor pump parameters. Throughout treatment, monitor the pump settings to ensure pump is working and that unauthorized or accidental changes in pump parameters have not occurred.

Figure 19:
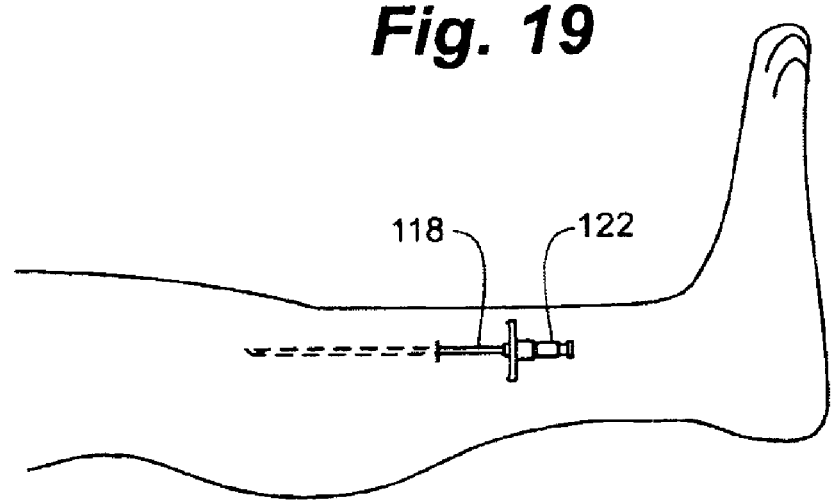
Figure 20:
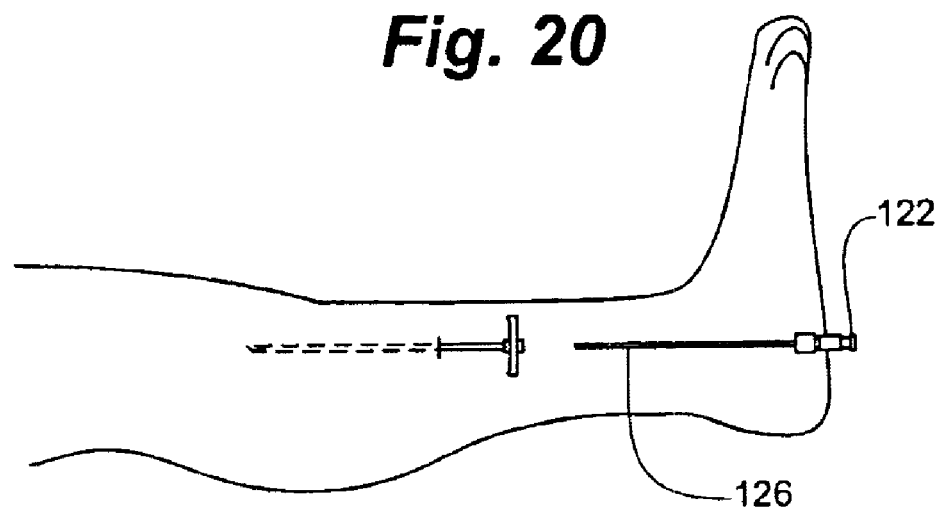

Insert the introducer into the muscle compartment. Prepare the skin surface at point of insertion using standard antiseptic methods. Remove the introducer's protective cover and insert the introducer into the site of therapy. Avoid excessive bending or manipulation of the introducer during insertion to minimize distortion of sheath when the trocar is removed. (See FIG. 19). Care should be taken when inserting introducer to avoid any nerves or large blood vessels in vicinity of treatment site. If considered necessary, verify the introducer position using fluoroscopy or other suitable means. Remove the trocar by slowly twisting the trocar hub to disengage from the sheath hub and then gently removing the trocar 126 and disposing of according to normal procedures. (See FIG. 20).

Insert the catheter by removing and disposing of the protective cover from the catheter. Carefully insert the catheter's tip into the sheath hub. Care should be taken during insertion to ensure that the slit tubing at the catheter's tip is not damaged or distorted. Continue inserting the catheter into the sheath until the silicone tubing on the catheter touches the sheath hub. This will place the distal tip of the catheter approximately 2 to 3 mm from the distal end of the sheath. Since the slit tubing tip and hollow fiber bundle are fragile, care should be taken when inserting the catheter into the sheath.

Figure 21A:
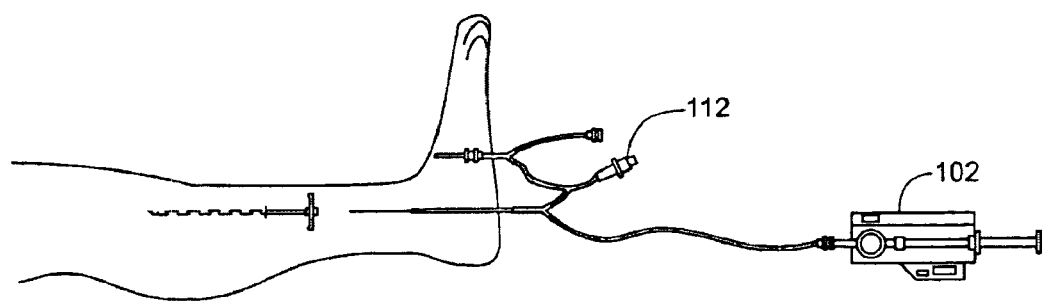
Figure 21B:
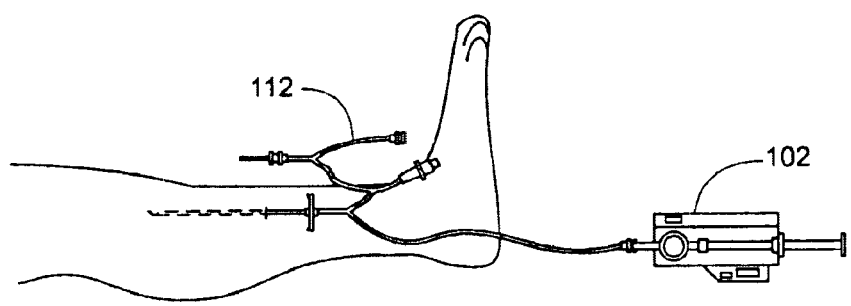

Remove the tear-away sheath. With the catheter in desired position, gently break the sheath hub and begin pulling the sheath out. As the sheath is removed, continue to tear apart the sheath while holding the catheter in place. Two people may be necessary to ensure a steady catheter position during sheath removal. Dispose of the separated sheath using standard practice. (See FIG. 21). If the catheter is not located in desired location, remove the catheter and reinsert the introducer to reposition the catheter at new location.

Maintain the indwelling catheter, using typical standard of care for indwelling catheters at the catheter entrance site. Stabilize the catheter shaft to prevent excessive bending which could kink catheter. After visually confirming that the catheter has been properly placed, position the silicone tubing to prevent kicking.

Position the pressure monitor and syringe reservoir. Position the pressure monitor according to instructions included with monitor. Position the syringe with plunger handle pointing down and near the insertion site, and affix to the body using tape. To ensure accurate pressure reading, the pressure monitor's transducer diaphragm must be positioned at same height as the tip of the catheter.

Connect the vacuum line by connecting the vacuum extension line to the male luer connector on the catheter vacuum line. Next connect the vacuum extension line to the vacuum pump connector. Prime the connecting line with saline. Pressure can be monitored at any time. To ensure patency, inject less than 3/10 cc of saline into the compartment. Refer to the Stryker Instructions for Use. Record the pressure reading, waiting for the display to reach equilibrium. At the doctor's discretion record the pressure reading at timed intervals.

Remove interstitial fluid by turning on the pump and verifying that the vent cap is attached. Continue therapy for a desired period of time (e.g., up to 72 hrs). Continue therapy until muscle compartment pressure is stabilized at acceptable level. During the course of therapy, monitor the fluid drip rate into the syringe reservoir. Remove and replace the syringe whenever 1 to 2 ml of fluid is collected.

Remove and replace the syringe by opening the vent and removing the cap from the vent portion to release vacuum. Aspirate the vacuum line by pulling back the syringe plunger to remove fluid lying in tubing between the vent and syringe. Remove and cap the syringe for analysis of its contents. Immediately attach a new sterile 3 cc syringe and replace the vent cap to continue fluid removal.

Remove the catheter by gently pulling straight back. Set aside and allow vacuum to continue draining. If any resistance is met when retracting the catheter, inject up to ½ ml of saline and attempt removal again. If resistance is still met, leave the device in place for 30 minutes without vacuum, and attempt removal again. Clean the puncture site and apply dressing according to standard procedures, continue standard puncture wound therapy at the therapy site. Dispose of the catheter set using standard practice.

A system such as that shown in FIGS. 5–11 can be used with the following protocol and instructions in order to treat sites at risk for cerebral edema. Prepare the catheter and system by opening the associated packaging while maintaining sterility. The catheter can be placed intracranially by several options at the discretion of the clinician using components found in FIG. 10. Determine the desired site of therapy. The catheter can be placed directly into brain parenchyma with the pressure-monitoring tip placed within the cerebral ventricles.

Position the pressure line and monitor according to instructions. Caution: To ensure accurate pressure reading, ensure that the pressure monitor's transducer diaphragm is positioned at same height as the tip of the catheter. Connect the vacuum line by attaching the vacuum extension line to the catheter vacuum line. Connect the vacuum extension line to the vacuum pump connector. An optional fluid trap including syringe collection chamber and desiccant cartridge may be included in the vacuum line to measure fluid removal. In conditions of high humidity, an optional air desiccator can be used. Remove the air filter from the air intake line and attached the desiccant cartridge using sterile technique. Replace the air filter on the intake of the desiccant cartridge.

A. Monitor Intracranial Pressure
  1) Pressure can be monitored at any time.
  2) Record Pressure Reading. Wait for the display to reach equilibrium. Record the pressure reading at the appropriate intervals.

B. Remove Edema Fluid
  1) Turn on pump or other vacuum source. Confirm flow of air through the air intake.
  2) Monitor fluid collection. During the course of therapy, fluid may accumulate in the syringe and desiccant. Remove the fluid in syringe or replace desiccant when necessary.
  3) Replace optional air intake desiccant cartridge as necessary.

C. Termination of Treatment

Clinicians will determine the appropriate time for termination of treatment based on severity of injury and response to treatment. Remove the catheter assembly by gently removing the catheter by pulling straight back. Set aside and allow vacuum to continue draining.

What is claimed is:

1. A therapeutic system for the treatment of tissue swelling, the system comprising:
   a) one or more recovery catheters implantable within then body and comprising semipermeable membranes,
   b) recovery components for recovering bulk fluid or fluid components through the semipermeable membranes and from the tissue site, in order to achieve a therapeutic result, preferably in the form of a reduction in swelling, and
   c) a hydratable medium comprising a hydratable gas adapted to be used directly or indirectly with the tissue site and within the semipermeable membrane(s) under conditions suitable to remove water from the tissue site in the form of hydrated medium.

2. A system according to claim 1 wherein the system further comprises monitoring components associated in an integral manner with the recovery catheter(s) and adapted to qualitatively and/or quantitatively assess one or more parameters in a substantially real time fashion.

3. A system according to claim 2 wherein the parameters are selected from the group consisting of physiologic parameters associated with the tissue itself and performance parameters associated with the function of the system or its components.

4. A system according to claim 3 wherein the physiologic parameters are selected from the group consisting of tissue pressure, blood flow, hydration, temperature, pH, and biochemical parameters.

5. A system according to claim 4 wherein the monitoring components are associated with the system in that that one or more components of the monitoring components are physically and/or functionally integrated with the placement and/or operation of the semipermeable membrane component.

6. A system according to claim 5 wherein the system comprises the delivery of a hydratable gas to the recovery catheters and further comprises the use of a pressure monitor component associated with the recovery catheters in a single, implantable catheter assembly.

7. A system according to claim 6 comprising a recovery catheters that comprises a plurality of hollow fibers formed of semipermeable membranes selected from the group consisting of polyacrylonitrile, polyethersulfone, cellulose and polysulfone, each having an outer diameters between about 0.1 mm and about 10 mm and providing permeability in the range of from about 1 kD to about 200 microns.

8. A system according to claim 7 wherein the system further comprises a sterile kit of introducer components selected from the group consisting of burr hole drill adapted to form a hole within the skull of a patient exhibiting cerebral edema, a tunneling trocar adapted to provide a path for the catheter assembly to pass through the burr hole and to a tissue site, and a placement stylet adapted to fit within the catheter assembly in order to position it within the tissue site.

9. A system according to claim 1 wherein the recovery catheter(s) comprise a plurality of hollow fibers formed of semipermeable membranes.

10. A system according to claim 9 wherein the fibers are formed of materials selected from the group consisting of polyacrylonitrile, polyethersulfone, cellulose and polysulfone.

11. A system according to claim 10 wherein the fibers have outer diameters between about 0.1 mm and about 10 mm and provide permeability in the range of from about 1 kD to about 200 microns.

12. A system according to claim 11 wherein the outer diameters are between about 0.3 mm and about 1 mm, and provide permeability in the range from about 50 kD and about one micron.

13. A system according to claim 12 further comprising one or more introducing components are selected from the group consisting of introducers, sytlets, and trocars, and combinations thereof.

14. A system according to claim 9 wherein the recovery components are adapted to control the movement of fluid by means selected from the group consisting of 1) the movement of interstitial fluid within the tissue itself, 2) the movement of fluid from the tissue and into a semipermeable membrane(s) positioned therein, and 3) the movement of fluid from or within the lumen of the hollow fibers.

15. A system according to claim 14 wherein the recovery components comprises a combination of negative hydrostatic pressure, for removal of fluid from the lumen of the hollow fibers and diffusion, for the movement of fluid from the tissue and into the semipermeable membrane(s).

16. A system according to claim 15 wherein the diffusion is accomplished by the delivery of a dehydrated medium into the semipermeable membrane(s) under conditions suitable to permit the tissue to hydrate the medium upon the passage of water vapor through the membrane walls.

17. A therapeutic system for the treatment of tissue swelling, the system comprising:
   a) one or more recovery catheters comprising semipermeable membranes,
   b) introducing components adapted to position the recovery catheter(s) within a tissue site exhibiting swelling,
   c) recovery components for recovering bulk fluid or fluid components through the semipermeable membranes and from the tissue site, in order to achieve a reduction in swelling,
   d) a hydratable medium comprising a hydratable gas adapted to be delivered to the tissue site and within the semipermeable membrane(s) under conditions suitable to remove water from the tissue site in the form of hydrated medium, and
   e) monitoring components associated with the recovery catheter(s) and adapted to monitor one or more physiologic parameters selected from the group consisting of tissue pressure, blood flow, hydration, temperature, pH, and biochemical parameters,
   wherein the system is adapted for the treatment of compartment syndrome or cerebral edema, the recovery components comprise a combination of negative hydrostatic pressure and diffusion adapted to control the movement of fluid from the tissue and into the semipermeable membranes, and negative hydrostatic pressure adapted to remove fluid from within the lumen of the membranes and from the tissue site.

18. A method of treating a tissue site exhibiting swell, the method comprising the step of providing a system according to claim 1 and employing the system to remove fluid from the tissue site exhibiting swelling, or from a tissue site physiologically associated with the tissue site exhibiting swelling.

19. A method according to claim 18 comprising a recovery catheter that comprises a plurality of hollow fibers formed of semipermeable membranes.

20. A method according to claim 19 wherein the fibers are formed of materials selected from the group consisting of polyacrylonitrile, polyethersulfone, cellulose and polysulfone.

21. A method according to claim 20 wherein the fibers have outer diameters between about 0.1 mm and about 10 mm and provide permeability in the range of from about 1 kD to about 200 microns.

22. A method according to claim 21 wherein the outer diameters are between about 0.3 mm and about 1 mm, and provide permeability in the range from about 50 kD and about one micron.

23. A method according to claim 18 wherein the system is adapted for the treatment of compartment syndrome.

24. A method according to claim 18 wherein the system is adapted for the treatment of cerebral edema.

25. A method of preparing a therapeutic system for the treatment of tissue swelling, the method comprising the steps of assembling a system comprising:

a) one or more recovery catheters implantable within the body and comprising semipermeable membranes, b) recovery components for recovering bulk fluid or fluid components (e.g., water) through the semipermeable membranes and from the tissue site, in order to achieve a therapeutic result, preferably in the form of a reduction in swelling, and c) a hydratable medium comprising a hydratable gas adapted to be delivered to the tissue site and within the semipermeable membrane(s) under conditions suitable to remove water from the tissue site in the form of hydrated medium.

26. A method according to claim 25 wherein the system is adapted for the treatment of compartment syndrome.

27. A method according to claim 25 wherein the system is adapted for the treatment of cerebral edema.

28. A method according to claim 25 comprising a recovery catheters that comprise a plurality of hollow fibers formed of semipermeable membranes.

* * * * *